United States Patent

Ramaswamy

[11] Patent Number: 5,260,437
[45] Date of Patent: Nov. 9, 1993

[54] RECOVERY OF CAFFEINE FROM TEA TRIMMINGS AND VEGETABLE WASTES

[75] Inventor: Setlur R. Ramaswamy, Louisville, Ky.

[73] Assignee: PepsiCo, Inc., Purchase, N.Y.

[21] Appl. No.: 981,015

[22] Filed: Nov. 24, 1992

[51] Int. Cl.$^5$ .............................. C07D 473/12
[52] U.S. Cl. ..................... 544/274; 544/275
[58] Field of Search .................. 544/274, 275

[56] References Cited

U.S. PATENT DOCUMENTS

| | | | |
|---|---|---|---|
| 716,878 | 12/1902 | Faunce | 544/274 |
| 1,273,054 | 7/1918 | Fontanelli | 544/274 |
| 2,422,874 | 6/1947 | Zenlea | 544/274 |
| 2,472,881 | 6/1949 | Bender | 544/274 |
| 4,673,743 | 6/1987 | Wilkens | 544/274 |

Primary Examiner—Mukund J. Shah
Assistant Examiner—Pavanaram K. Sripada
Attorney, Agent, or Firm—Scully, Scott, Murphy & Presser

[57] ABSTRACT

Tea trimmings and wastes are dried and then burned either directly or indirectly to liberate caffeine which is recovery by water scrubbing or electrostatic precipitation. The crude caffeine is then concentrated and purified by crystallization for use in foods and pharmaceuticals.

13 Claims, 3 Drawing Sheets

RECOVERY OF CAFFEINE FROM TEA TRIMMINGS AND VEGETABLE WASTES

This invention relates to recovering caffeine from caffeine containing vegetable waste and more particularly to the burning of tea pruning waste and recovery of caffeine from the combustion product.

DESCRIPTION OF PRIOR ART

In preparing tea, coffee and cocoa for beverage use, the vegetative waste from the growing of these materials is ordinarily returned to the soil or otherwise disposed of as waste. For example, in the management of tea gardens, the tea bushes are periodically stripped of their entire foliage for purposes of rejuvenating the tea bush. The pruned leaves are presently buried in soil. Wastes from tea factories such as stems, stalks and dust are also discarded. The waste from the tea factory and pruning operation have no value for beverages and contain up to 2.5% caffeine on dry basis. Similar treatment is made of other waste contain appreciable amounts of caffeine.

U.S. Pat. No. 4,673,743 to Wilkens discloses a process for separating caffeine from caffeine-loaded activated carbon by sweeping an inert gas through the carbon to recover caffeine without burning the carbon. The caffeine containing gas is then quenched with cold water to recover the caffeine.

U.S Pat. No. 716,878 to Faunce discloses a method of separating caffeine from coffee waste which may contain up to 8% caffeine by first separating some caffeine and oil by heating a vessel containing the coffee waste and condensing the volatilized oils and caffeine. The heat decomposes the vegetable matter into insoluble carbon and gases. The carbon remaining in the vessel contains a considerable amount of caffeine which is recovered by placing the charred material in boiling water to extract the caffeine. The water is evaporated leaving crystalline caffeine.

U.S. Pat. No. 1,273,054 to Fontanelli teaches a process of subliming caffeine from soot and deposits recovered from flues of coffee roasters by indirectly heating the soot to vaporize the caffeine, removing the caffeine with gas passing over the soot and, thereafter, condensing the caffeine on cooler surface walls of the equipment.

U.S. Pat. No. 2,422,874 to Zenlea teaches a process for heating cocoa waste such as shells to recover water, theobromine, tar and carbon. The theobromine is recovered by crystallization.

SUMMARY OF THE INVENTION

We employ dry waste caffeine material as the heat source used to volatilize caffeine and the smoke from the resulting combustion as the carrier to transport the caffeine to a suitable scrubber which recovers the caffeine for subsequent purification.

We have found that dried caffeine containing waste material, particularly waste dried tea bush leaves may be subjected to a controlled combustion and pyrolysis in a current of air. The resulting gaseous combustion product contains most of the caffeine is contacted with water to recover the caffeine. The tea leaves are either converted to carbon by indirect heating using carbon recovered from this process, or to ash by direct burning of the dry leaves. When indirectly heating the leaves either air, an inert gas or vacuum recovery of caffeine may be employed. Direct burning of the dried leaves in air is the least capital intensive means of recovering caffeine. The caffeine is purified by crystallization from water or from an alcoholic aqueous solution.

DETAILED DESCRIPTION OF THE INVENTION

The process consists of first drying waste caffeine containing material such as pruned waste tea leaves by exposing the material to the sun under dry conditions or where economically possible using heated air driers employing heat which may be generated by burning some of the carbon recovered from this process.

The dried caffeine containing material is next introduced into a suitable furnace where the dry material is pyrolysed or burned in a controlled fashion. Direct combustion furnaces can be employed to generate hot air to dry the freshly recovered caffeine containing material such as tea prunings or to generate steam for heat or process use. The smoke from such direct burning furnaces is then conducted through, preferably water scrubbers, where water is circulated over packing or sprayed over the combustion gas to remove caffeine. The smoke, after passing through one or more scrubbers in series is discharged to the atmosphere. The caffeine laden scrubber water is recovered and evaporated to produce a crude caffeine solution or solid. If desired the solution can be dried by suitable drumdrier or the like to solid crude caffeine.

The process may also be carried out using indirect heat to burn or pyrolye the dried caffeine containing material. The dried material may be burned in hearth or moving grate type furnaces or in fluidized bed systems and the caffeine recovered from the combustion gases. Alternatively, the dried material may be burned in a closed tank and combustion gases recovered using vacuum to draw the gas through a caffeine scrubber.

Figure 1:
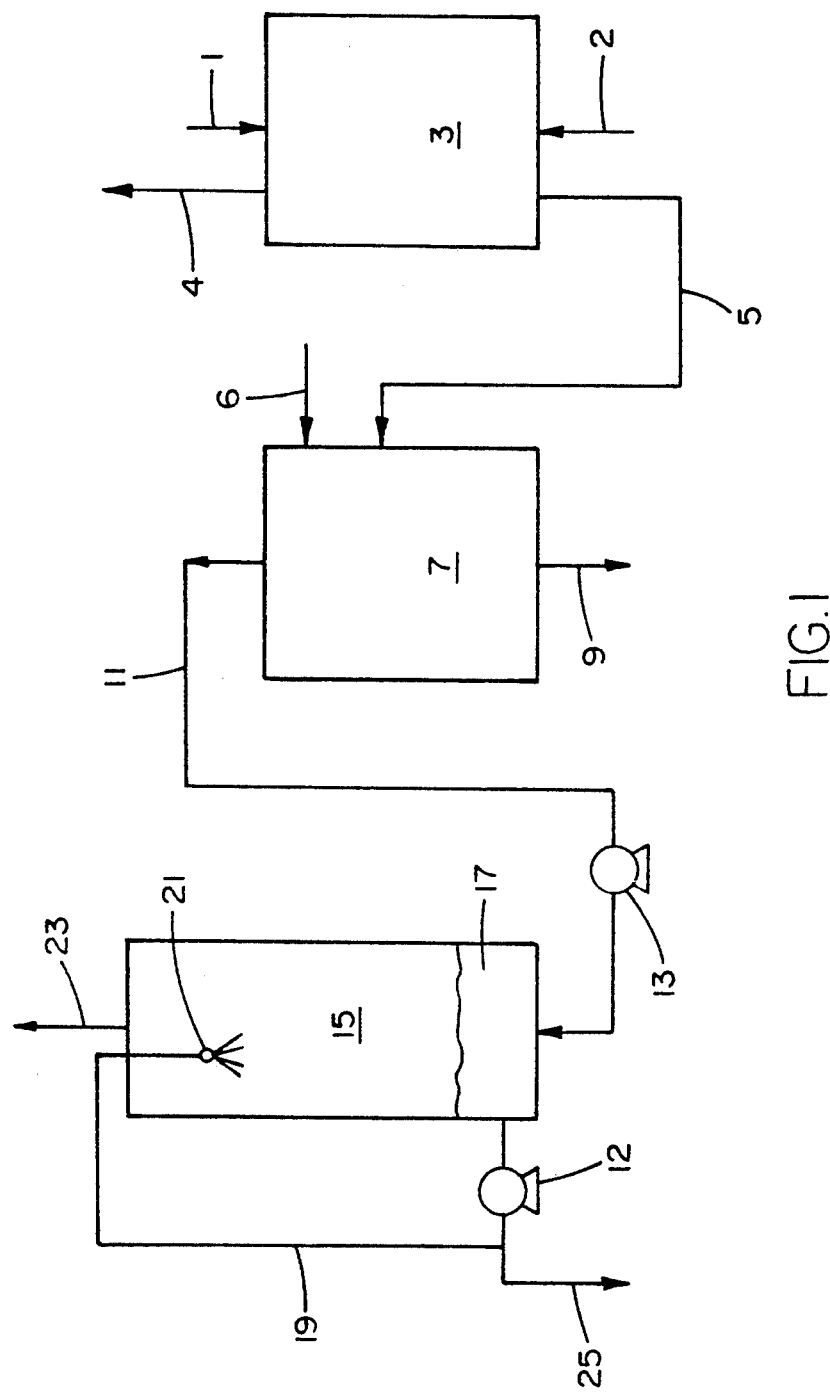
FIG. 1 is a block diagram illustrating direct burning of caffeine containing material to recover caffeine.

Reference is now made to the figures which are block diagrams of the processes of this invention. FIG. 1 shows a hot air tea drier 3 which receives waste tea bush trimmings 1. Warm air 2 is passed over and through the trimmings to lower the moisture content to below 20% moisture, preferably below 15% moisture. The moist air is discharged at 4. When dry, the tea trimmings are conveyed 5 to a conventional furnace 7 where the dried tea is burned in an atmosphere of air 6. Ash 9 is removed periodically. The combustion products enter a stack at 11 and are transported by means of a blower 13 to the bottom of a scrubber 15. The combustion products rise up the scrubber and exit at 23. Recycled solutions or water is sprayed 21 over the combustion products and passes down through the baffled or packed scrubber 15. Pump 12 removes solution containing the caffeine which has been separated from the combustion products. Solution 17 may be recycled 19 to increase the concentration of caffeine. Solution recovered at 25 is concentrated and purified for use in foods and pharmaceuticals.

Figure 2:
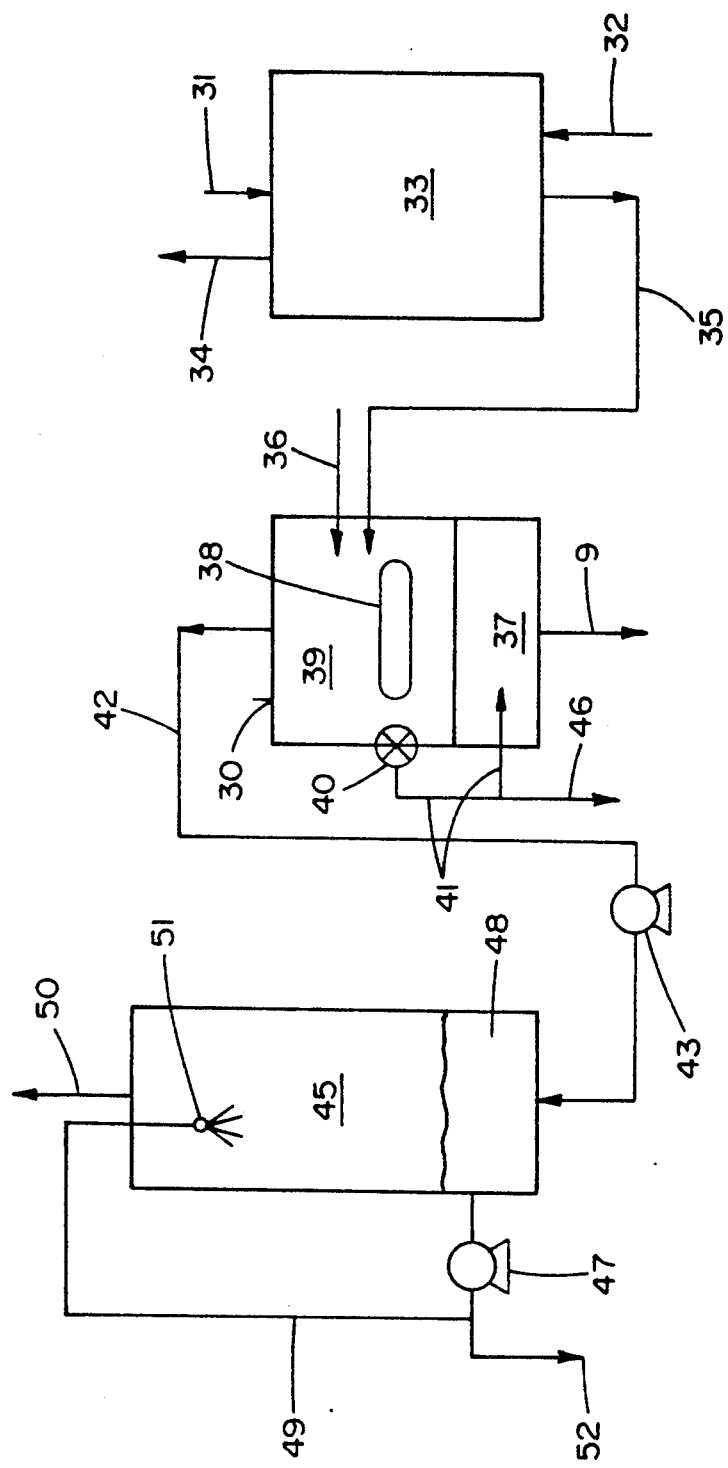
FIG. 2 is a block diagram illustrating indirect burning of caffeine containing material to recover caffeine and charcoal.

Now turning to FIG. 2 there is shown a diagram for indirect burning of waste tea. The tea 31 is introduced to a suitable drier 33 such as a tray or grain drier and warm air 32 is passed over and through the tea to dry it to below 15% moisture, preferably below 10% moisture. Moist air is discharged from the drier at 34. The dry tea is conveyed 35 to an indirect furnace 30 where air or inert gas 36 is introduced to sweep combustion products to the stack 42. The tea is conveyed 38 through the furnace chamber 39 and discharged through a rotary lock 40 as charcoal 41 suitable for heating the furnace in fire box 37 or recovered for other process heating needs at 46. The combustion gases are blown into the bottom of a scrubber 45 using fan 43. Water or caffeine solution is sprayed 51 over the combustion gases as they rise in the scrubber and are discharged at 50. Caffeine solution 48 is pumped from the scrubber using pump 47 and recycled through line 49 to the scrubber spray system 51. Caffeine solution is recovered at 52 and concentrated and/or purified for food and pharmaceutical use.

Figure 3:
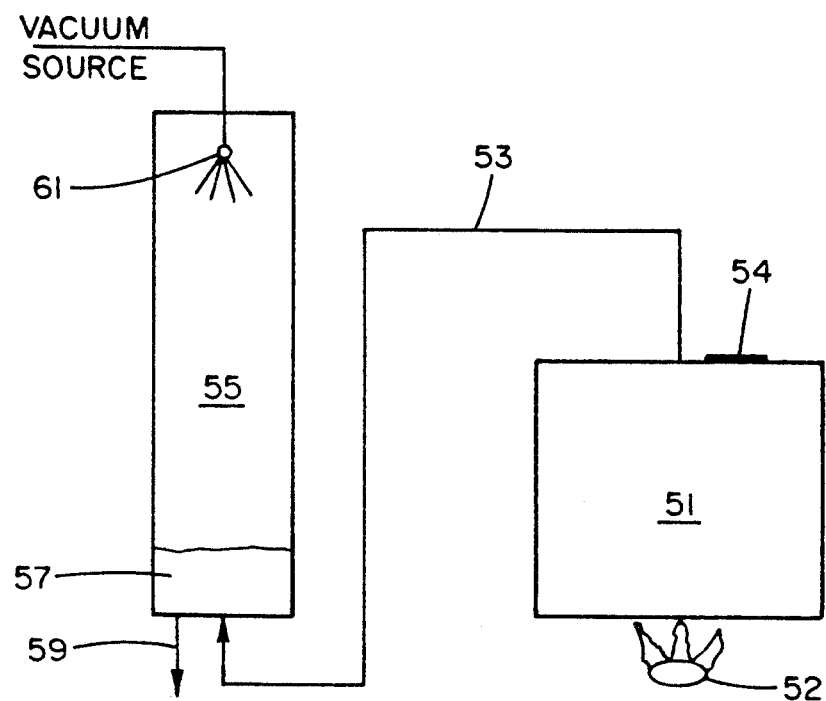
FIG. 3 is a block diagram illustrating indirect burning of caffeine containing material and recovery of caffeine by a vacuum.

FIG. 3 shows an indirect combustion chamber 51 which is filled with previously dried tea (not shown). The tea is dried in a manner illustrated in FIGS. 1 and 2 or any alternative means of drying vegetable material. The tea (not shown) in vessel 51 is heated by gas flame 52 or other suitable heat source and generates combustion products containing caffeine which are withdrawn from the vessel 51 through line 53 to a suitable scrubber 55 and then to a suitable vacuum source such as a mechanical pump, a venturi type of vacuum system or other known vacuum generating devices. As the composition gas passes up through the scrubber 55, it contacts water 57 sprayed down the column from nozzle 61. If desired the column can be packed or baffled to increase separation efficiency. In any case, the water sprayed from 61 strips caffeine from the combustion gases and is recovered at 59 for concentration and purification. After burning the dry tea, the resulting carbon in vessel 51 can be recovered through cleaning out 54.

Multiple scrubbers may be employed in a counter current manner to improve the recovery of the caffeine.

The caffeine may be recovered in any suitable smoke scrubber such as packed towers, impingement scrubbers or dry scrubbers such as electrostatic scrubbers, condensers or fume filters.

The caffeine can later be purified by dissolving in hot water, using activated carbon or other suitable adsorbents to remove impurities and then removing the carbon by filtration. The filtrate is cooled to crystallize the caffeine. Repeated crystallizations and purifications may be made. We prefer to employ alcoholic solution, usually pure methanol to crystallize the caffeine. Impurities in the crude caffeine can also be recovered by dissolving the caffeine in a solvent that does not have an affinity for the impurities such as a chlorinated hydrocarbon and then redissolving the caffeine in water and crystallizing out the caffeine.

We prefer to burn the caffeine containing material using heat generated from the material by preferably directly burning the dried material or indirectly by burning the carbon resulting from indirect burning. We prefer to recover the caffeine in a wet scrubber, to concentrate the scrubber water containing the caffeine and to purify the caffeine by crystallization from alcoholic solution.

The process of this invention employs controlled burning or pyrolysis at 300° C.–450° C., preferably 350° C.–400° C. to sublime the caffeine from the burning material into a gas steam of combustion products when directly burning, or combustion products including a carrier gas or vacuum driven gas during indirect burning to carry the caffeine from the burning material to the caffeine recovery equipment, usually wet scrubbers. By recycling scrubber water and then evaporating the solution one can recover a crude caffeine solution of 20–25% caffeine. This crude solution is the purified by dissolving in 100% alcoholic (methanol) solution at ambient temperature and then cooling to below 0° C., preferably below −10° C. to recover the caffeine as pure crystals. The crystals are easily filtered from the cool solution and dried to yield pure caffeine suitable for food or pharmaceutical use.

The process is further described but not limited by the following examples.

EXAMPLE 1

A glass tube 625 mm long and 50 mm in diameter is packed with 250 gms of black tea. The bottom of this tube is connected to a water cooled condenser, flask and a gas scrubber containing about 100 cc of water. A vacuum pump is connected to the scrubber and air is drawn through the bed of tea leaves. The top surface of the tea leaves in the packed tube is ignited. As the leaves burn the fire zone descends down the tube and dense white fumes are formed. The fumes pass through the condenser and condense into a dark brown colored liquid. Uncondensables pass into the gas scrubber and caffeine and other water soluble substances are trapped in the water contained in the scrubber. About 140 gms of liquid result from mixing the scrubber liquid and the condensate. The mixture is evaporated to about 30 gm of tarry material with a caffeine content of 20–25%. This material is then purified by dissolving in hot 100% methanol, the solution cooled to precipitate the caffeine, the caffeine filtered from the solution and dried. Recrystallizations can be conducted to improve the purity of the caffeine.

In a modification of this experiment, additional black tea is continuously fed to the top surface of the tea leaves so that the fire zone remains continuously burning in the tube. In such a case, water is periodically or continuously added and removed from the scrubber to insure as much caffeine is recovered as is possible.

EXAMPLE 2

Tea leaves are placed in a 2 liter 3 necked glass flask. Through one neck a lead in tube is introduced to carry in a stream of nitrogen or air. From the second neck the gases are taken out and passed through the condenser and scrubber described in example 1. Through the third neck a thermometer is introduced for recording the temperature. The flask is immersed in a fluidized sand bath which is electrically heated. The bath temperature is brought up to 350° C.–400° C. Nitrogen or air rates of about 2 liters/minute are used. Dense white fumes are obtained, which on condensing, scrubbing and concentrating as in example 1 yield a product containing about 20–25% caffeine. A black char is left in the flask. The char can be used as a heating medium for the dried tea waste or to dry the tea waste prior to burning.

A vacuum can be employed rather than the nitrogen or air to pull the dense white fumes from the flask onto the scrubber where caffeine is recovered. The char can be recovered and used for heating.

Activated carbon can be made by employing inert gas and steam in the flask to activate the carbon which can be sold for water purification or other uses. The caffeine containing combustion products are removed using vacuum as discussed previously.

What is claimed is:

1. A process of recovering caffeine from caffeine containing waste material comprising:
   a) drying the waste to a combustible condition;
   b) burning the waste to form gaseous combustion products including caffeine;
   c) stripping crude caffeine from the gaseous combustion products into water to form a solution of said caffeine; and
   d) purifying the caffeine from said solution by crystallization.

2. The process of claim 1 in which the waste material is tea bush prunings.

3. The process of claim 2 in which the tea prunings are burned in air contacting the prunings.

4. The process of claim 3 in which the air and combustion products containing caffeine is passed through a scrubber wherein water is employed to recover the caffeine as an aqueous solution from the combustion products.

5. The process of claim 4 wherein the scrubbed gas is discharged and the caffeine solution is concentrated by evaporation.

6. The process of claim 4 wherein the caffeine is purified by crystallization from alcohol.

7. The process of claim 4 wherein the caffeine is crystallized several times to purify the caffeine.

8. The process of claim 2 wherein the prunings are burned using indirect heat.

9. The process of claim 8 wherein the caffeine contained in combustion products resulting from indirect burning is recovered in a scrubber 10. The process of claim 9 wherein the combustion products are moved to the scrubber in inert gas.

11. The process of claim 9 wherein the combustion products are moved to the scrubber using a vacuum.

12. The process of claim 9 in which the prunings are burned using indirect heat supplied by charcoal previously recovered from indirectly burning the caffeine containing material.

13. The process of claim 9 wherein the combustion products are moved to the scrubber in air.

* * * * *